US00PP14903P2

(12) United States Plant Patent
Fear et al.

(10) Patent No.: US PP14,903 P2
(45) Date of Patent: Jun. 15, 2004

(54) RASPBERRY PLANT NAMED 'DRISCOLL CARDINAL'

(50) Latin Name: *Rubus idaeus L.*
Varietal Denomination: Driscoll Cardinal

(75) Inventors: Carlos D. Fear, Aptos, CA (US); Richard E. Harrison, Aptos, CA (US); Fred M. Cook, Aptos, CA (US); Gavin Sills, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 37 days.

(21) Appl. No.: 10/306,452

(22) Filed: Nov. 27, 2002

(51) Int. Cl.[7] ..... A01H 5/00
(52) U.S. Cl. ..... Plt./204
(58) Field of Search ..... Plt./204

*Primary Examiner*—Bruce R. Campell
*Assistant Examiner*—Susan B. McCormick
(74) *Attorney, Agent, or Firm*—Pennie & Edmonds LLP

(57) ABSTRACT

The present invention relates to a new and distinct cultivar of raspberry plant named Driscoll Cardinal. The new cultivar is distinguished from other raspberry cultivars by its firm and very consistent fruit with regard to its size and shape throughout its harvest period. The new cultivar is distinguished from its seed parent by having larger fruit and more vigorous canes; it is distinguished from its pollen parent by producing a higher yield of fruit and better flavored fruit.

3 Drawing Sheets

Latin name of the genus and species of the plant claimed: The variety is botanically identified as *Rubus idaeus* L.

1. BACKGROUND OF THE INVENTION

The new cultivar of raspberry plant was developed from the hybridization of the selection 'M48.9' (an unpatented variety) as the seed parent with the selection 'Gloria' (U.S. Plant Pat. No. 11,067) as the pollen parent. The parents were crossed in 1994, whereafter fruit and seed were collected to produce seedlings for field planting in Carpenteria, Calif. in 1995. The new cultivar was selected from these seedlings in 1995 for its excellent attractive firm fruit. The new cultivar has been asexually propagated by in vitro shoot tip culture, root sucker division and root cuttings at the Cassin Ranch in Santa Cruz County, Calif. and has been shown to maintain the desired and distinguishing characteristics after propagation over several generations.

2. SUMMARY OF THE INVENTION

The present invention provides a new and distinct cultivar of red raspberry plant named 'Driscoll Cardinal'. The cultivar is botanically identified as *Rubus idaeus* L. The 'Driscoll Cardinal' red raspberry plant produces a primocane crop which begins in mid-July and continues until mid-October. The floricane crop begins in mid-May and continues until mid-July. Both the primocane and floricane yields are high relative to other comparable varieties. The fruit of 'Driscoll Cardinal' is notably quite firm and very consistent with regard to its size and shape throughout its harvest period. The fruit of 'Driscoll Cardinal' separates easily from its receptacle.

3. BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics.

4. DETAILED BOTANICAL DESCRIPTION

Figure 1:
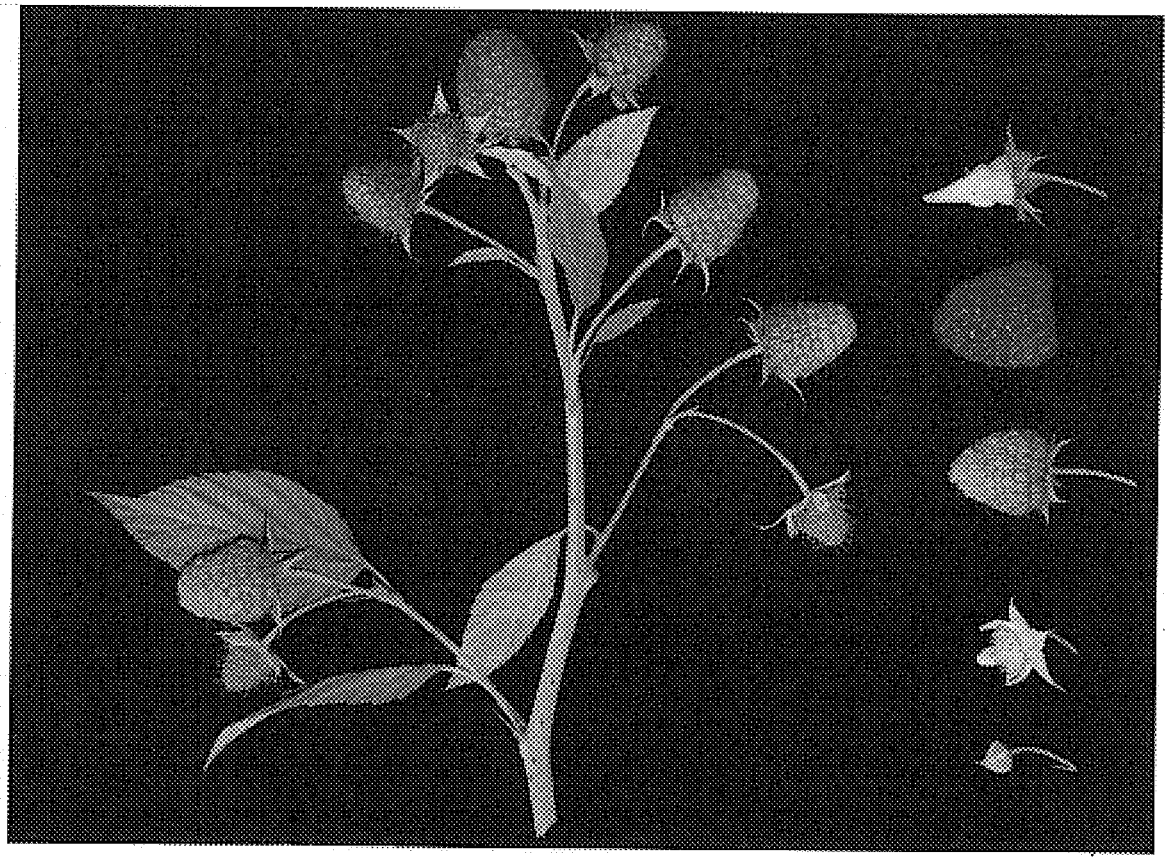
FIG. 1 is a photograph of 'Driscoll Cardinal' primocane flower fruit in various stages of development.
Figure 2:
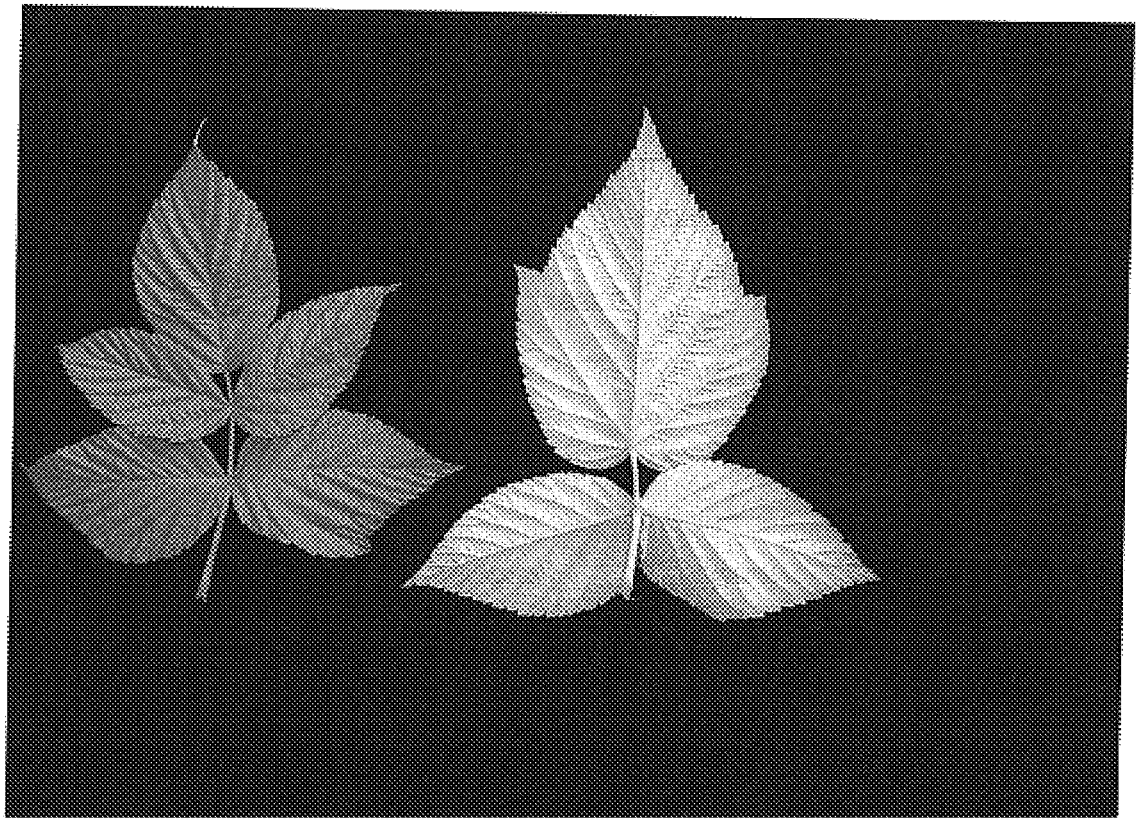
FIG. 2 is a photograph of 'Driscoll Cardinal' primocane leaves showing upper and lower leaf surfaces.
Figure 3:
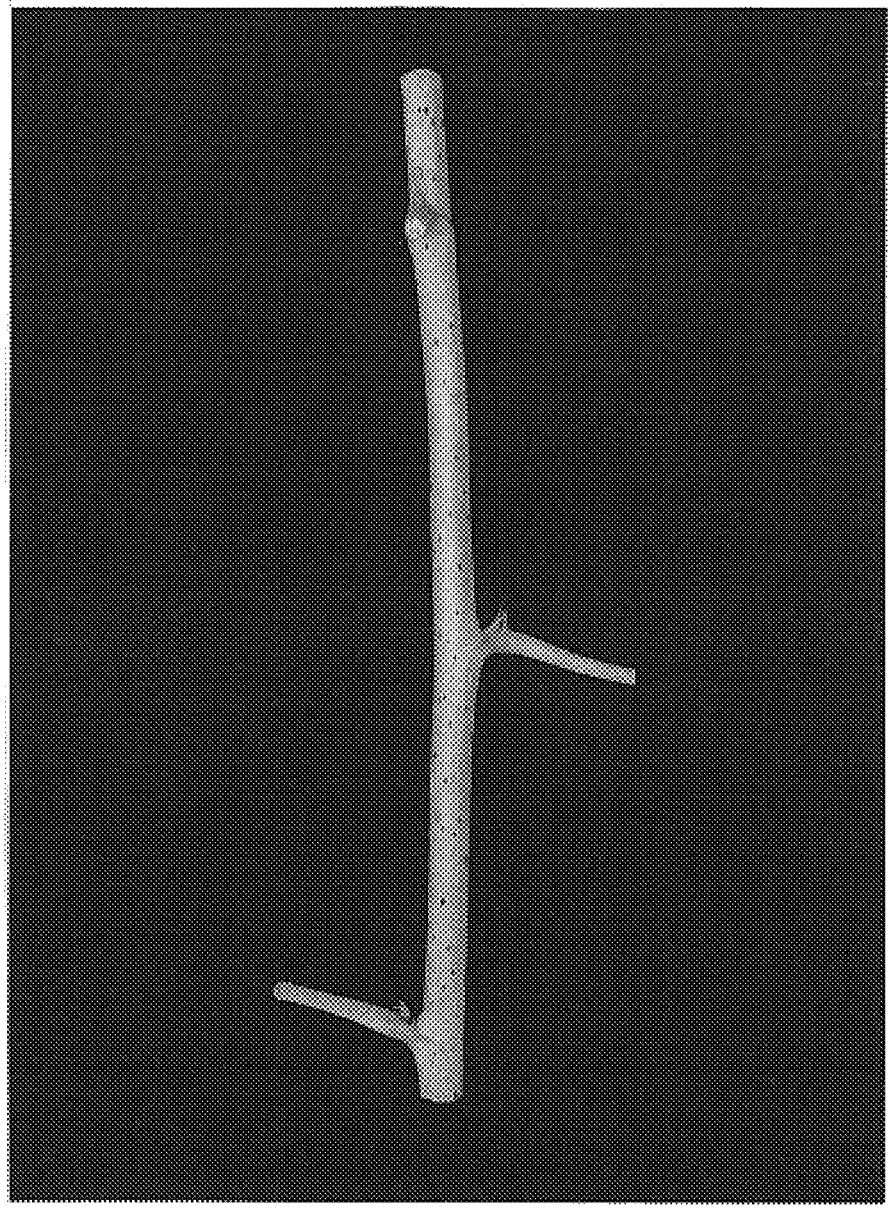
FIG. 3 is a photograph of 'Driscoll Cardinal' primocane shoot.

The following detailed description of the new raspberry cultivar, 'Driscoll Cardinal', is based upon observations taken of 7 to 17 month old plants and fruit grown in Watsonville, Calif. between 2001 and 2002, and is believed to apply to plants of the 'Driscoll Cardinal' cultivar grown in similar conditions of soil and climate elsewhere.

Throughout this specification, color names beginning with a small letter signify that the name of the color, as used in common speech, is aptly descriptive. Color data followed by an alphanumeric code designates the color according to The R.H.S. Colour Chart published by The Royal Horticultural Society of London, England. Color designations, color descriptions, and other phenotypical descriptions may deviate from the stated values and descriptions depending upon variation in environmental, seasonal, climatic and cultural conditions.

Table 1 provides information on the plant and fruit characteristics of the new cultivar 'Driscoll Cardinal' compared with characteristics of the unpatented raspberry cultivar 'Heritage'. Observations of the cultivars were taken under similar conditions.

The new variety is particularly characterized and distinguished from other cultivars by its fruit firmness, consistent fruit structure and high yield.

The fruit color of 'Driscoll Cardinal' is a medium red at harvest but darkens slightly after harvest to a deeper color. Fruit of 'Driscoll Cardinal' separates easily from the receptacle and is of excellent firmness at harvest. The fruit of 'Driscoll Cardinal' is very consistent in size and shape throughout the harvest period. The average plant height is about 200 cm and the average plant spread is about 80 cm. The prickle pigmentation color is 187A. The pedicel pigmentation color is 144A. The pigmentation color of the young shoots is 144A in color and the average number of young shoots per plant is 17.

The reproductive organs of 'Driscoll Cardinal' are variable. The pigmentation color of both surfaces of the petals is 155D and there are five petals per flower. The style pigmentation color is 157D, the average number of styles per flower is about 100, the anther pigmentation color is 155D, and the average number of anthers per flower is about 108. The color of the seeds of 'Driscoll Cardinal' is 161A, the average seed weight is about 1.2 mg, and there are an average of about 94 seeds per fruit.

The primocane and floricane yields of 'Driscoll Cardinal' are high relative to the variety 'Heritage'.

'Driscoll Cardinal' is distinguishable from its pollen parent, selection 'Gloria', by producing a higher yield of fruit and better flavored fruit. The new cultivar is distinguished from its seed parent, selection 'M48.9', by having larger fruit and more vigorous canes.

4.1 DISEASE AND STRESS RESISTANCE

Resistance is unknown to powdery mildew and root rots. Cold tolerance of the new cultivar has not been established. Post harvest fruit rot resistance is good in comparison over many selections and varieties.

TABLE 1

PLANT CHARACTERISTICS OF 'DRISCOLL CARDINAL'

| | Driscoll Cardinal | Heritage |
|---|---|---|
| General | | |
| Plant size | small-med | Large |
| Growth habit | erect | erect |
| Productivity | High | Medium |
| Self-fruitfulness | Self-fruitful | Self-fruitful |
| Time of bud burst | late | late |
| Primocane fruiting | | |
| Percent of cane length flowering as primocane | 30-40 | 20-40 |
| Percent of total yield | 51 | 53 |
| Primocanes | | |
| Number of young shoots | many | medium |
| Young shoot pigmentation | medium | medium |
| Length (cm) | 2.00 | 1.96 |
| Time of shoot emergence | early | very late |
| Glaucosity (waxy bloom) | weak | weak |
| Strength | medium | medium |
| Cane cross section from mid cane of primocane) | rounded | rounded |
| Dormant cane color | dark brown w/quite a lot of purple | brown to purple brown |
| Prickles | | |
| Pigmentation | brown to purple | green-brownish to green |
| Density on young shoots | medium | dense |
| Attitude of tip | downward | downward |
| Size: Length (base to tip at 1 m height at end of harvest) (mm) | 1 | 2.3 |
| Texture | smooth | rigid |
| Presence and distribution on petioles | present, irregularly | present irregularly |

TABLE 1-continued

PLANT CHARACTERISTICS OF 'DRISCOLL CARDINAL'

| | Driscoll Cardinal | Heritage |
|---|---|---|
| | | distribtuted |
| Pubescence on canes | absent | absent |
| Internodal distance (cm) (at central ⅓ of cane) | 6.5 | 5.3 |
| LEAVES | | |
| Color | | |
| Face | 147A | 147A |
| Underside | 148C | 148B |
| Relief between veins | weak | very weak |
| Glossiness | medium | medium |
| Petiole length (cm) | 5.4 | 7.6 |
| Stipule orientation | erect | erect |
| Arrangement | compound | compound |
| Number of leaflets | sometimes 3, sometimes 5 | sometimes 3, sometimes 5 |
| Overlapping of lateral leaflets | touching | free to touching |
| Lateral leaflet: length of stalket (lower pair) | short | very short |
| Terminal leaflet | | |
| Length (cm) | 10.7 | 14.6 |
| Width (cm) | 6.8 | 7.8 |
| Shape | ovate | ovate |
| Tip | acuminate | acuminate |
| Base | round | acute to rounded |
| Margin | doubly serrate | doubly serrate |
| Lateral leaflets (basal pair) | | |
| Length (cm) | 9.4 | 14.7 |
| Width | 6.6 | 8.6 |
| Orientation | opposite | opposite |
| Shape | ovate | ovate |
| Tip | acuminate | acuminate |
| Base | round | oblique |
| Margin | doubly serrate | doubly serrate |
| Rachis length between terminal leaflet and adjacent lateral leaflets (cm) | 3.4 | 1.5 |
| FLOWERS | | |
| Flowering period | | |
| Primocane | 15 weeks early June–mid-September | 19 weeks late May–late September |
| Floricane | 12 weeks, late March–late June | 10 weeks, late March–mid June |
| Flower diameter (cm) | 1.5 | 1.8 |
| Petal | | |
| Length (cm) | 0.9 | 0.8 |
| Width (cm) | 0.4 | 0.3 |
| Pedicel coloration | medium | Present, strong intensity |
| FRUIT | | |
| Harvest season | | |
| Primocane | mid-July–early Oct | Early July–early November |
| Floricane | mid-May–late July | Late May–late July |
| Fruting lateral | | |
| Length (4th lateral from tip) (cm) | 68.6 | 49.8 |
| Number of fruit per lateral | 19 | 20.3 |
| Color | | |
| Immature | 44D | 42C |
| Maturing | 46A | 46A |
| Mature fruit | 53A | 59A |
| Glossiness | weak | medium |
| Shape | ovate | ovate |

TABLE 1-continued

| PLANT CHARACTERISTICS OF 'DRISCOLL CARDINAL' | | |
|---|---|---|
| | Driscoll Cardinal | Heritage |
| Dimensions | | |
| Size | medium | small |
| Length | 20 | 17 |
| Width | 20 | 18 |
| Length:width | 1.0 | 0.94 |
| Weight (g/fruit) | | |
| Primocane | 4.1 | 3.1 |
| Floricane | 3.8 | 2.3 |
| Soluble solids (%) | 10.3 | 10.8 |
| Titratable acidity (% as citric acid) | 1.60 | 1.58 |
| Seed Weight (mg) | 2.3 | 1.5 |
| Number druplets/fruit | 94 | 72 |
| Adherence to plug | medium | medium |
| Firmness | med-firm to firm | Firm |
| Yield | high | medium |

4.2 NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531–5). Using a variety of oligonucleotide primers, alone or in combination, RAPD analysis of Driscoll Cardinal and Heritage yielded DNA fragment patterns that uniquely distinguish each of these genetically distinct genotypes.

We claim:

1. A new and distinctive cultivar of raspberry plant, substantially as shown and described.

* * * * *